United States Patent [19]

Dombrowski et al.

[11] Patent Number: 5,767,413

[45] Date of Patent: Jun. 16, 1998

[54] PERIPHERAL GAUGE

[75] Inventors: Valerie D. Dombrowski, Elkton, Md.; Lon M. Stevens, Huntsville, Ala.; Boyd D. Bryner, Brigham City, Utah

[73] Assignee: The United States of America as represented by the Secretary of the Air Force, Washington, D.C.

[21] Appl. No.: 657,726

[22] Filed: May 30, 1996

[51] Int. Cl.⁶ .............................. G01N 3/08; H01C 10/02
[52] U.S. Cl. .................................. 73/774; 73/826; 338/80
[58] Field of Search ........................ 73/774, 826; 338/80, 338/114

[56] References Cited

U.S. PATENT DOCUMENTS

| | | |
|---|---|---|
| 2,518,906 | 8/1950 | Kocmich ................................ 73/774 X |
| 2,562,749 | 7/1951 | Speer. |
| 3,210,993 | 10/1965 | Shoor et al. ................................. 73/774 |
| 3,290,521 | 12/1966 | Coleman et al. ...................... 338/80 X |
| 3,304,528 | 2/1967 | Rastrelli et al. ...................... 338/114 X |
| 3,332,280 | 7/1967 | Fish et al. ................................... 73/774 |
| 3,820,529 | 6/1974 | Gause et al. ........................... 73/774 X |
| 4,461,085 | 7/1984 | Dewar et al. ................................ 33/174 |
| 5,086,785 | 2/1992 | Gentile et al. ............................ 128/782 |

*Primary Examiner*—George M. Dombroske
*Assistant Examiner*—Paul D. Amrozowicz
*Attorney, Agent, or Firm*—Thomas C. Stover

[57] ABSTRACT

A gauge for measuring a dimensional change, such as a change in the periphery of a test object, is an elastomeric tube filled with an electrically conductive fluid such as mercury. The gauge can be formed into a loop around the test object. Thereafter, any change in, e.g. the circumference of the test object is monitored by measuring the change in resistance (or voltage) between the ends of the tube.

18 Claims, 2 Drawing Sheets

$R_1 = 120 \Omega$
$R_2 = 120 \Omega$
$R_3 = 120 \Omega$
$R_C = 116 \Omega$
$R_{10}$ = MERCURY GUAGE = e.g. 4 $\Omega$

PERIPHERAL GAUGE

STATEMENT OF GOVERNMENT INTEREST

The invention described herein may be manufactured and used by or for the Government for governmental purposes without the payment of any royalty thereon.

FIELD OF THE INVENTION

This invention relates to the field of physical measurements. More particularly, it relates to a gauge for accurately measuring the peripheral change of a specimen under test.

BACKGROUND OF THE INVENTION

One of the material characteristics of interest to engineers and designers is Poisson's ratio (or coefficient). This is the ratio of the lateral contraction to proportional stretching when an elastic material is under longitudinal strain. In order to determine Poisson's ratio, the specimen's initial height and diameter are measured. The specimen is then stretched by applying tension. Poisson's ratio can thereupon be determined from the tensile force applied during a testing cycle, the longitudinal displacement of the specimen, and the corresponding decrease in diameter of the specimen.

It is often desired to measure Poisson's ratio versus strain. One way to do this has been to provide a specimen in the form of a thin disk or "poker chip". Such specimen might be, for example, 3.5 inches in diameter and 0.35 inches in thickness (or height). The major surfaces of the chip are then bonded to two chuck faces which are then pulled apart to provide the required longitudinal displacement. A critical measurement made during this test is the reduction in diameter of the specimen. Until now, the method used for measuring diameter change has been to take photographs during the test sequence. However, using this method, it has only been possible to achieve diameter estimates to approximately the nearest three hundredths (0.03) of an inch. The problems associated with the photographic method are parallax, human error in diameter measurements along with the time required to read the measurements.

A prior art method which determines diameter by measuring circumferential change is disclosed in U.S. Pat. No. 2,562,749 to Speer. However, the device disclosed by Speer is a purely mechanical one believed incapable of achieving the desired accuracies.

By "periphery", as used herein, is included "circumference".

SUMMARY OF THE INVENTION

Broadly the present invention provides an apparatus for measuring the change in periphery of a body under test. The apparatus has; a) an elastomeric tube terminating in solid conductors at each end and b) a conductive fluid within and substantially filling the tube and contacting the solid conductors. The tube is adapted to wrap in a stretch-fit about the periphery of the body to be tested in an elastic loop, so that the tube will change its length as the body reduces or expands in periphery. Also provided are means for measuring the change in electrical resistance of the fluid to derive changes in the length of the tube in response to changes in the periphery of the body.

In a preferred embodiment of the present invention, a peripheral gauge is provided which includes a thin elastomeric tube which is formed into a loop slightly smaller than the original pheriphery (e.g., circumference) of the test specimen. The tube is filled with a conductive fluid such as mercury and includes an electrical lead at each end in contact with the mercury. The gauge is stretched like a rubber band and placed around the periphery of the test specimen, e.g. a chip. Thereafter, the resistance of the mercury column between the ends of the tube is measured throughout the test cycle. The change in the length of the loop (and of the column) is a function of the change in periphery (or circumference) of the test specimen.

By employing the gauge of this invention, it is possible to read peripheral or circumference measurements to the thousandths (0.001) of an inch with a calculated gauge error of less than 1% full scale.

For example, the tube is stretched around the chip in a loop, overlapping end portions are adhered together and the chip is axially pulled and necks down to a lesser circumference or periphery. This causes the loop to contract its conductive path and lower its resistance which can be read as a change in circumference (or other periphery), as described below.

BRIEF DESCRIPTION OF THE DRAWINGS

The invention will become more apparent from the following detailed specification and drawings in which.

DESCRIPTION OF PREFERRED EMBODIMENTS

Figure 1:
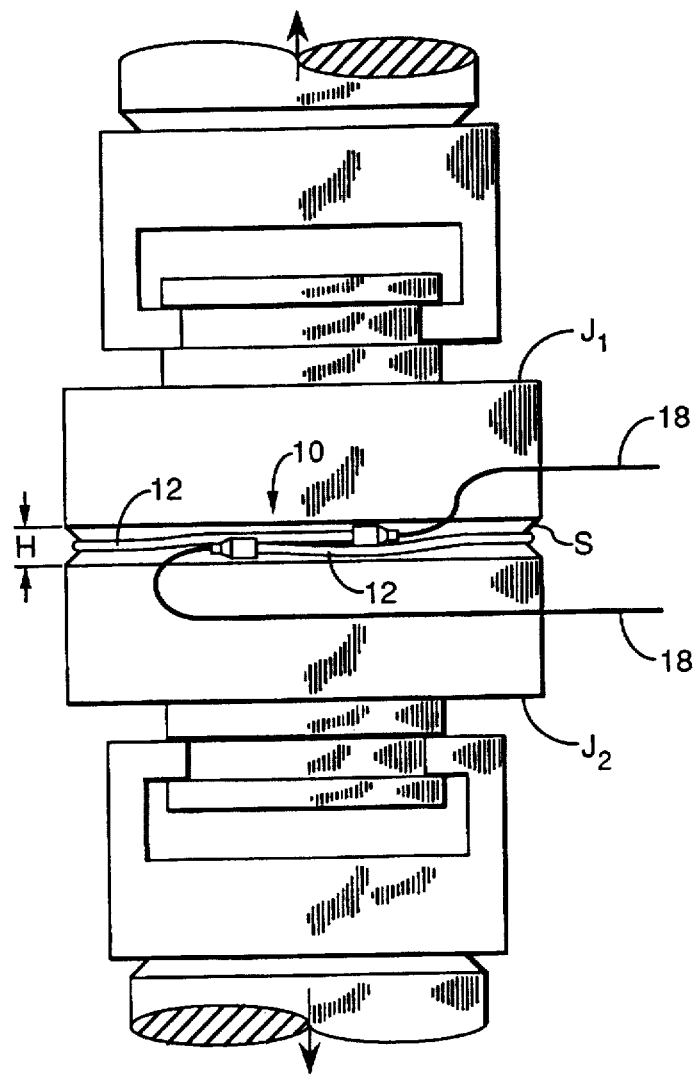
FIG. 1 is an elevational view of a specimen under test with the gauge of this invention in position for testing.

Referring in more detail to the drawings, per FIG. 1, there is illustrated a disk shaped specimen S which has been bonded to the two jaws J1, J2 of a test apparatus designed to apply tension as illustrated by the arrows. Gauge 10 of the invention, encircles the specimen. In the illustration of FIG. 1, tension is already being applied to the specimen S, resulting in its sidewall being necked down and concave, rather than cylindrical.

The construction of the gauge 10 of the invention can be best explained by reference to FIGS. 2 and 3. It includes a silicone tube 12 which, in one embodiment, has an outer diameter of 0.08 inch, an inner bore diameter of 0.02 inch, and a length of 10.75 inches. The tube 12 is filled with a conductive fluid, eg. mercury 14.

The two ends of the gauge 10 are similarly formed to seal in the mercury and provide electrical connections. Accordingly, only one end is illustrated in the enlarged detail of FIG. 3. A stranded lead wire 16, having an insulating coating 18, is soldered or otherwise secured to a pair of twisted platinum endpins 20. One of the twisted endpins is terminated, leaving a single axial platinum endpin 22 extending into the mercury 14. The bared lead wire 16 and the twisted endpins 20 are coated with an electrically insulating paste 24 and inserted into an insulating sleeve 26, which may be, for example, of polytetrafluoroethylene (PTFE). This sleeve, in turn, is inserted into the end of the tube 12. A thread 28 is tied tightly about the end of the tube to prevent the escape of mercury. Plastic tubing 30 is shrunk onto the end of the tube 12 and the insulating coating 18 of the lead wire 16.

Figure 2:
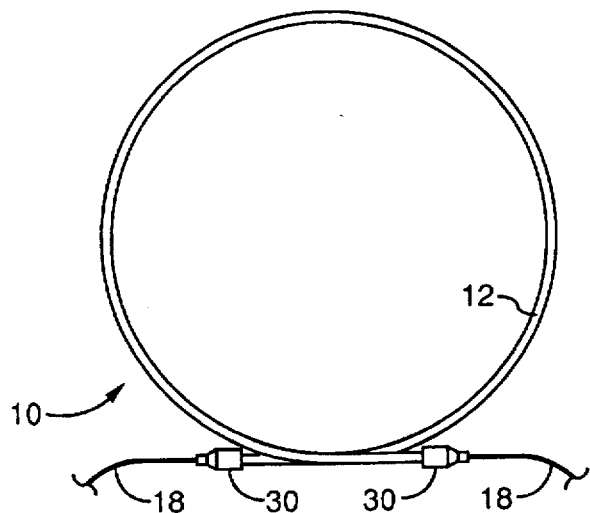
FIG. 2 is a schematic plan view of a gauge constructed in accordance with the invention.
Figure 3:
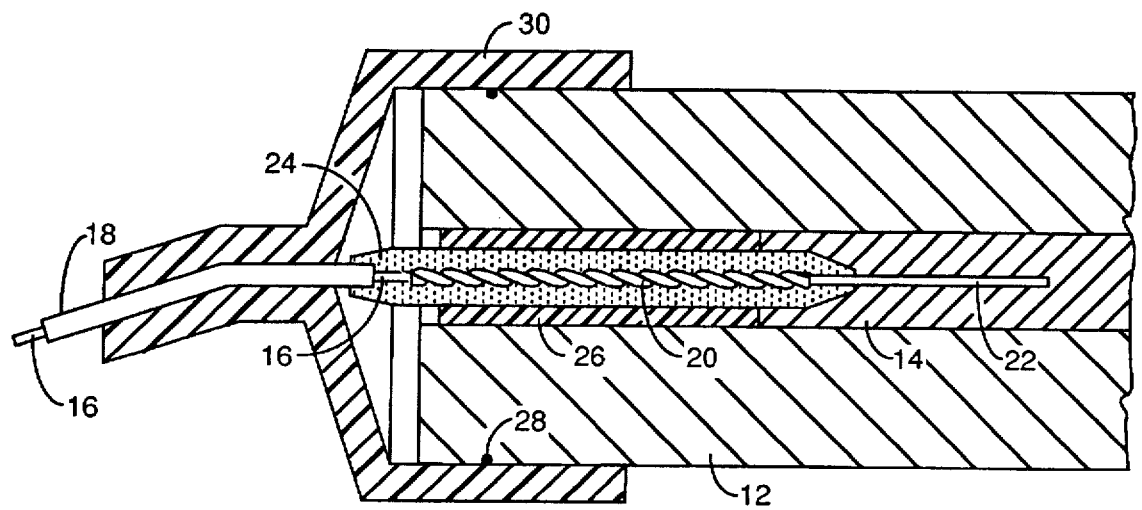
FIG. 3 is an enlarged detail, in cross-section, of one end of the gauge of the invention

After construction of the gauge 10, by filling with mercury and completing the ends as described, it is shaped into a loop as shown in FIG. 2 and the ends cemented together. The inside diameter of the loop should be less than the outer diameter of the specimen S. In one example, for a specimen having an outer diameter of 3.50 in., the gauge 10 is set at an inside loop diameter of 3.365 in. and positioned over the circumference of the specimen in a stretch fit.

Thus to measure the circumferential changes of the cylindrical specimen, the gauge 10 is stretched and placed over the specimen S at its mid height, as shown in FIG. 1. Both the specimen and the gauge are lubricated in order to allow the gauge 10 to move to the location of minimum diameter as the specimen necks down due to loading.

Figure 4:
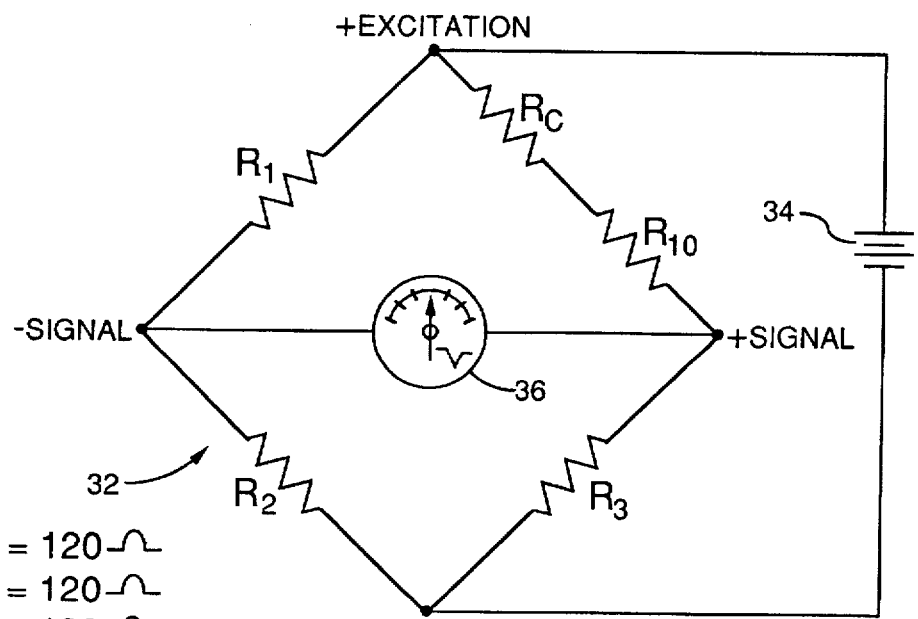
FIG. 4 is a schematic diagram of an electrical bridge circuit incorporating the gauge of the invention.

The gauge 10 is connected to a Wheatstone bridge 32, having DC power supply 34, as illustrated in the diagram of FIG. 4. In this diagram, the resistance of the gauge 10 is represented by resistor $R_{10}$, which is in series with resistance $R_c$. The resistance of each of $R_1$, $R_2$, & $R_3$ is, eg. 120 ohms and, when the gauge 10 is in its static state, $R_c+R_{10}$ equals, eg. 120 ohms. e.g. $R_c=116$ ohms and $R_{10}=4$ ohms. The gauge 10 is in its static state, e.g. when its loop is stretched around the periphery of the test specimen and the Wheatstone bridge 32 is in balance.

In operation, the resistance of gauge 10 changes, e.g. with its length, causing an imbalance in the Wheatstone bridge 32, which change is monitored by a voltmeter 36. The recorded voltage change is correlated to a physical change in the gauge's length, through use of a calibrated master curve. The calibrated master curve is generated by measuring the change in gauge millivolt output while moving the gauge loop over a graduated mandrel of known circumferences.

The following example is provided to illustrate the invention and should not be construed in limitation thereof

EXAMPLE I

A gauge constructed in accordance with this invention, was employed to measure Poisson's ratio versus strain of a 3.5 inches diameter, 0.35 inch thick disk shaped specimen of silica-filled nitride butadiene rubber (NBR). The gauge was constructed employing a silicone tube of 0.08 inch outside diameter and 0.02 inch inside diameter. The tube had a length of 10.75 inches. It was constructed as described above and its ends were cemented together to form a loop having an inside diameter of 3.365 inches.

The gauge became one element ($R_{10}$) in the Wheatstone bridge described above. An excitation voltage of 5 V. D.C. was applied to the bridge. The output of the bridge was signal conditioned and recorded using standard instrumentation practices as millivolts versus time. The circumference versus time (rate of separation of jaws J1 & J2) was determined by comparing the gauge millivolt output recorded during testing, to the above noted gauge calibration master curve. The gauge was able to read circumference measurements to the thousandths (0.001) of an inch and had a calculated gauge error of less than one per cent full scale.

As indicated in the above example, the starting height (thickness) of the test disk is noted, as is the pulling or separation rate between J1 & J2, from which the change in height of the pulled disc, delta H, can be calculated. These values are employed in known equations to calculate Poisson's ratio for the material (test disc). A discussion of such calculations is found in "Williams M. L. et al, *The Triaxial Tensile Behavior of Viscoelastic Materials.* GALCIT Report SM63-6, Feb. 1963, which Report is incorporated herein by reference.

What is claimed is:

1. An apparatus for measuring the change in periphery of a body under test which comprises:

a) an elastomeric tube terminating in solid conductors at each end, b) a conductive fluid within and substantially filling said tube and contacting said solid conductors, c) said tube being adapted to wrap in a stretch-fit about the periphery of a body to be tested in an elastic loop which is closed at overlapping tube portions and adhering said overlapping tube portions together so that only said loop will change its length as said body reduces or expands in periphery and d) means for measuring the change in electrical resistance of said fluid to derive changes in length of said tube in response to changes in the periphery of said body.

2. The apparatus of claim 1 wherein said tube is electrically non-conductive.

3. The apparatus of claim 1 wherein said tube measures peripheral changes as small as 0.001 in.

4. The apparatus of claim 1 wherein said loop has lubrication thereon.

5. The apparatus of claim 1 wherein said fluid is liquid mercury.

6. A gauge comprising:

a) an elastomeric tube terminating in solid conductors at each end, b) a conductive fluid within and substantially filling said tube and contacting said solid conductors, said tube forming a loop with overlapping portions, which overlapping portions are adhered together so that only said loop will change its length and c) means for measuring changes in the electrical resistance of said fluid to derive changes in the length of said tube.

7. The gauge of claim 6 wherein said tube is electrically non-conductive.

8. The gauge of claim 6 wherein said tube is elastomeric and measures change as small as 0.001 in.

9. The gauge of claim 6 wherein said fluid is liquid.

10. The gauge of claim 9 wherein said liquid is mercury.

11. The gauge of claim 10 wherein said tube is electrically non-conductive.

12. The gauge of claim, 6 wherein the measuring means comprises an electrical bridge circuit connected to said conductors.

13. A method for measuring changes in periphery of a body comprising:

a) wrapping an elastomeric tube in a stretch fit about the periphery of a body in an elastic loop which is closed at overlapping tube portions and adhering said overlapping tube portions together so that only said loop will change its length, said tube containing a conductive fluid within, b) applying a voltage across the length of said tube and c) measuring changes in electrical resistance of said fluid to derive changes in the length of said tube in response to changes in the periphery of said body.

14. The method of claim 13 wherein said changes in electrical resistance are measured by measuring the changes in voltage drop lengthwise across said tube as its length changes.

15. The method of claim 13 wherein said fluid is liquid.

16. The method of claim 15 wherein said liquid is mercury.

17. The method of claim 13 wherein said tube is wrapped about said body in a stretch fit.

18. The method of claim 14 wherein said tube has end portions which are fixed relative to each other.

* * * * *